United States Patent [19]
Lansing et al.

[11] Patent Number: 5,302,124
[45] Date of Patent: Apr. 12, 1994

[54] DISPOSABLE PROTECTIVE SLEEVE FOR DENTAL APPARATUS SUCH AS LIGHT CURING GUNS

[75] Inventors: Thomas A. Lansing, Pine Springs, Minn.; Paul Kuehn, Eau Claire, Wis.

[73] Assignee: Pinnacle Products, Inc., St. Paul, Minn.

[21] Appl. No.: 37,996

[22] Filed: Mar. 25, 1993

[51] Int. Cl.$^5$ .............................................. A61C 1/16
[52] U.S. Cl. .................................... 433/116; 433/29; 150/154
[58] Field of Search .................. 433/116, 29, 229; 604/171, 172; 128/16, 852, 856; 150/154, 161; 383/907; 118/504, 505; 362/804; 206/439

[56] References Cited
U.S. PATENT DOCUMENTS

| | | | |
|---|---|---|---|
| 1,742,061 | 12/1929 | Curry | 433/116 |
| 4,723,912 | 2/1988 | Nieusma | 433/116 |
| 4,777,574 | 10/1988 | Eisner | 362/399 |
| 4,795,343 | 1/1989 | Choisser | 433/116 |
| 4,795,669 | 1/1989 | Bowskill | 428/194 |
| 4,810,194 | 3/1989 | Snedden | 433/116 |
| 4,975,826 | 12/1990 | Bell | 362/376 |
| 4,976,616 | 12/1990 | Eisner | 433/77 |
| 5,142,736 | 9/1992 | Kuehn et al. | 116/111 R |
| 5,168,863 | 12/1992 | Kurtzer | 604/171 |

OTHER PUBLICATIONS

Advertising sheet published Feb. 1993 by Dental Disposables International in Dentistry Today, showing various products including a "Curing Light Sleeve" described as a disposable cover for curing light handles. Brochure by Pinnacle Products, Inc. published 1992, entitled "We Cover It All . . . With Innovative Barrier Protection."
Ash/Dentsply "Disposa Shield", a shield for a light handle T-bar for dentist lights.
Sample of product produced by Summit Protection Control Products and presently on the market in the United States.

Primary Examiner—Cary E. O'Connor
Attorney, Agent, or Firm—Foley & Lardner

[57] ABSTRACT

A disposable protective sleeve used for covering dental equipment such as light curing guns has two panels of flexible plastic which are joined together at a top edge and at side edges, the sleeve having an open bottom to allow the sleeve to be pulled over the equipment, for example, a light gun. Apertures are formed in the sleeve at opposite positions in the sleeve. The apertures may be defined by notches cut in the adjoining panels of the protective sleeve at positions along the side edges spaced from the top edge. When the protective sleeve is drawn onto a light gun, the front end of the body of the typically cylindrical light gun extends through one of the apertures of the sleeve, while the back end of the light gun, which is typically vented, extends through the other aperture. The protective sleeve covers the handle of the light gun where it is held by the dentist. After a procedure with a patient is completed, the protective sleeve is pulled off of the gun and disposed of, and a new protective sleeve is used before a procedure on another patient.

23 Claims, 4 Drawing Sheets

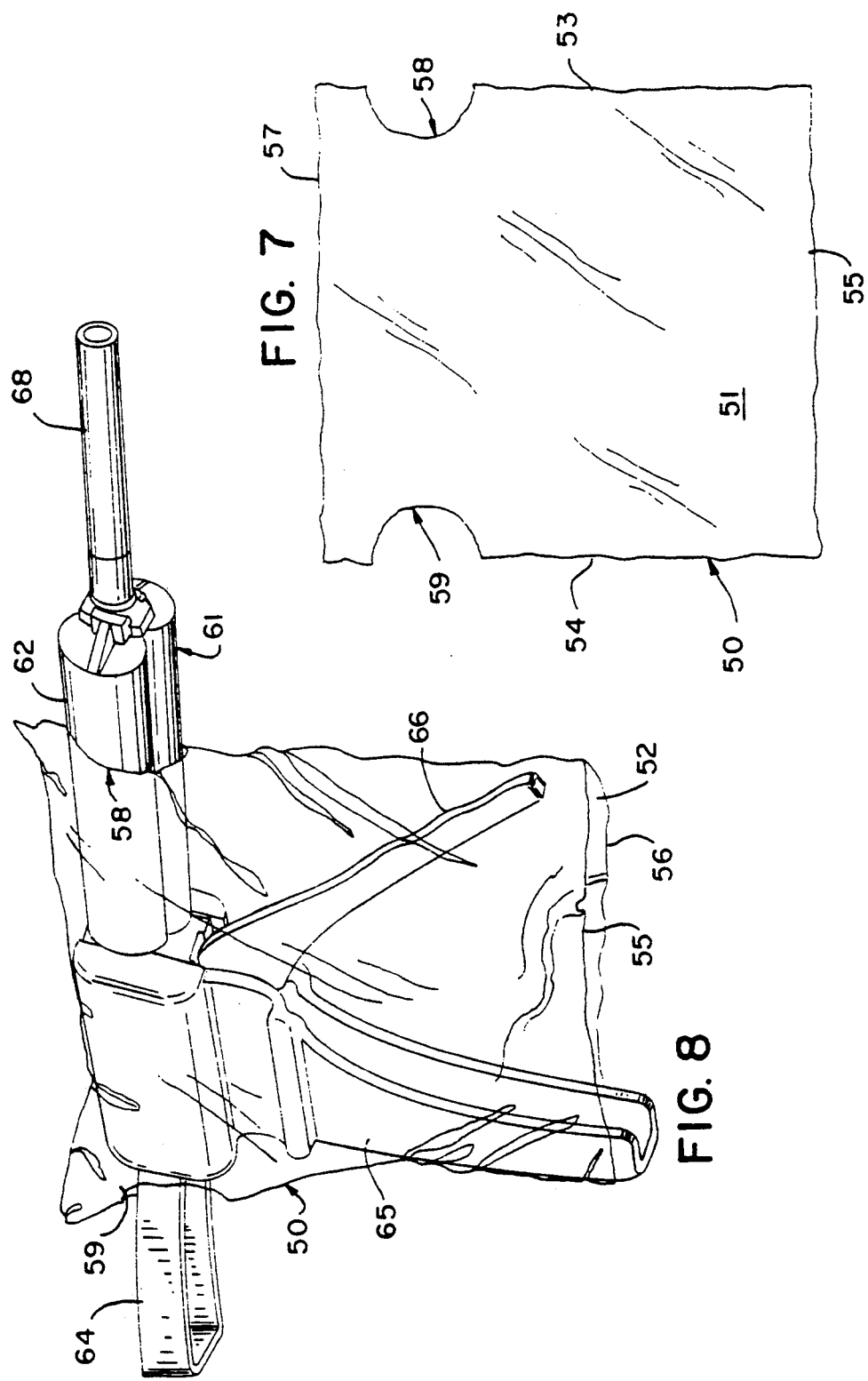

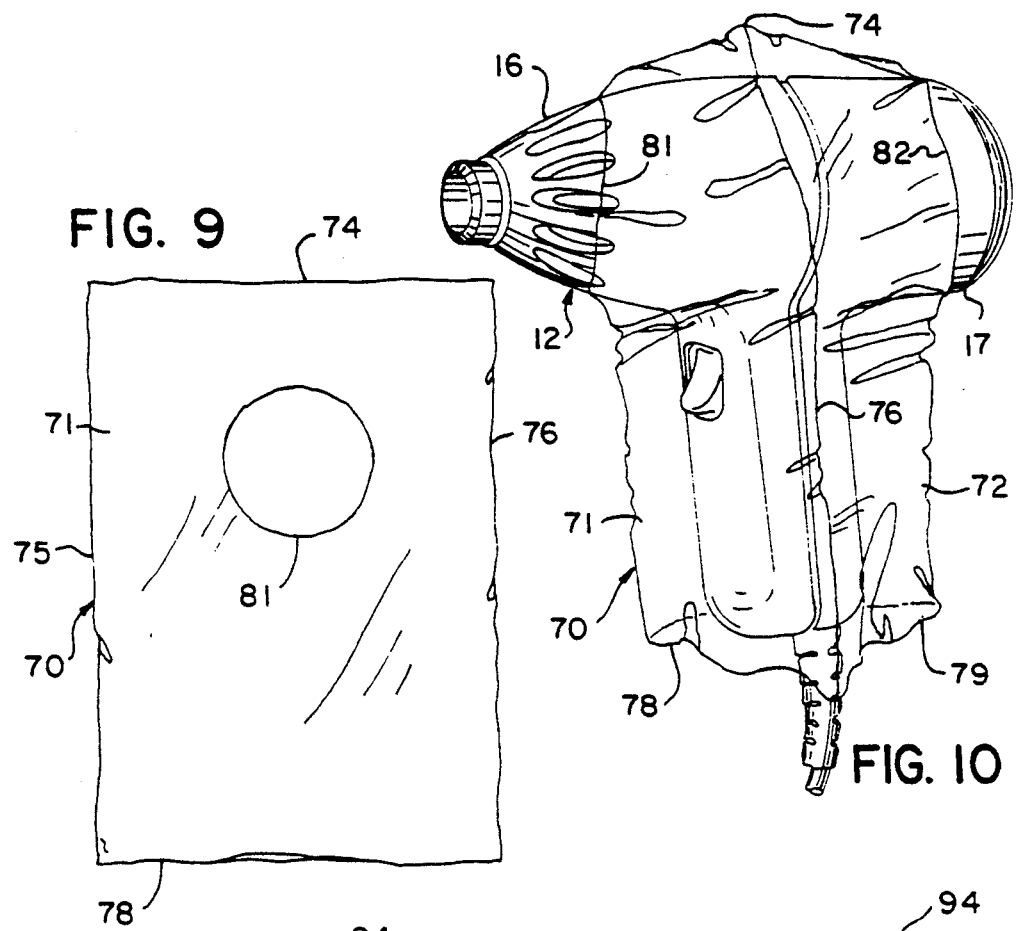
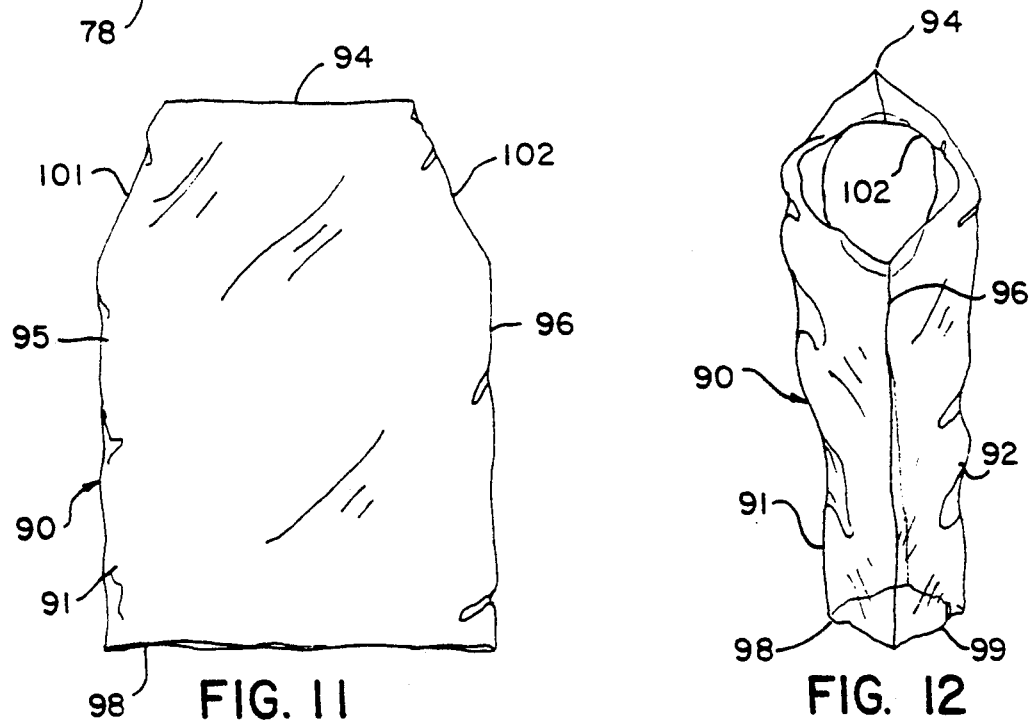

DISPOSABLE PROTECTIVE SLEEVE FOR DENTAL APPARATUS SUCH AS LIGHT CURING GUNS

FIELD OF THE INVENTION

This invention pertains generally to the field of protective covers for preventing the spread of infection, and more particularly to coverings for dental equipment such as light curing guns and the like.

BACKGROUND OF THE INVENTION

To help prevent the spread of biological contamination from one patient to another, where possible, dental instruments are sterilized after use with each patient. However, some devices handled by a dentist or hygienist during a procedure are not conveniently sterilized or are not capable of withstanding sterilization procedures. One example of such devices is the light curing gun used by dentists to apply light to light curable tooth repair materials. This is an electrical and optical device which cannot withstand autoclaving or other sterilization procedures. Another type of device used during procedures which is not readily sterilized is an impression material mixing gun, similar to a caulking gun, which is used to produce a homogeneous mix without hand mixing for dental impressions.

To attempt to minimize cross contamination between patients, dentists have sometimes wrapped these larger devices which cannot be sterilized in various wrapping materials, such as sheets of flexible plastic, e.g., Saran ® wrap, or in standard plastic bags. However, protecting the equipment in this manner is obviously inconvenient and less than satisfactory, since wrapping the equipment properly takes time, and during a procedure the wrapping may work loose to allow the equipment to be exposed, thereby defeating the purpose of the wrapping.

SUMMARY OF THE INVENTION

In accordance with the present invention, a protective sleeve for dental equipment is especially suited to be easily pulled onto hand held dental equipment such as light curing guns and putty guns to cover the portions of such equipment that would ordinarily be handled by the dentist, and to then be easily removed after the procedure with a patient is completed. The protective sleeve is formed of a low cost flexible plastic and can be produced from standard sheets of plastic material by simple heat sealing and die cutting operations. The protective sleeve thus formed is economically disposable after each use.

The protective sleeve of the invention in a preferred form has two flexible plastic film panels which are joined together at a top edge and also at two side edges, with the bottom edges of the panels being unjoined to provide an open bottom which allows access to the interior of the protective sleeve. Notches are formed in the panels to form two opposed apertures in the sleeve at positions adjacent the top edge. These apertures are preferably much closer to the top edge than to the bottom edges of the panels. In a preferred form, the notches are formed at each side edge to provide adjoining semi-circular or semi-elliptical openings in each of the panels, with the notches together providing a circular or elliptical aperture as the panels are pulled apart as the sleeve is drawn over the hand held equipment. The apertures may also be formed as opposed, preferably circular, openings cut into each panel at a position near the top edge, or by cutting off the top corners of the panels by a cut which extends from a side edge to the top edge.

The apertures are preferably sized to accommodate the front end and the back end of hand held equipment which extends forwardly and rearwardly from the handle portion of such equipment, as is typically the case with light curing guns and putty guns. This allows the forward end of the equipment, for example the light guide tube of the curing gun, to extend from the sleeve without interference, and also exposes the back end of the equipment without unduly distorting the sleeve, allowing the sleeve to fit relatively tightly over the equipment. For typical light curing guns, which conventionally have vent openings for cooling air, the second aperture of the protective sleeve allows the back end of the gun to be exposed to allow free admission of air into or exit of air from the vents of the gun. Nonetheless, the sleeve fits around the handle of the curing gun to completely cover it at all positions at which the dentist will grasp the handle, as well as covering adjacent portions of the body of the gun which might incidently be contacted by the hand of the dentist.

The protective sleeve of the present invention may be formed to specifically accommodate various shapes of hand held dental equipment, for example, by utilizing tapered panels so that the bottom edges of the panels are narrower than the top edge to more closely fit a handle, and can be made with wide top and bottom edges to accommodate other types of guns, such as putty guns, which have wider handles than light curing guns.

Further objects, features and advantages of the invention will be apparent from the following detailed description when taken in conjunction with the accompanying drawings.

BRIEF DESCRIPTION OF THE DRAWINGS

In the drawings:

FIG. 7 is a plan view of a protective sleeve adapted in size and shape to fit on a typical dentist's putty gun.

FIG. 8 is a perspective view of a protective sleeve of the invention shown placed on a putty gun.

FIG. 9 is a plan view of a protective sleeve of the invention having apertures formed in the middle of each panel at a position near the top edge.

FIG. 10 is an illustrative view of the protective sleeve of FIG. 9 drawn onto a light curing gun.

FIG. 11 is plan view of a protective sleeve of the invention having apertures formed by cuts in the panels extending from the side edges to the top edge.

FIG. 12 is an illustrative side view of the sleeve of FIG. 11 with the panels drawn apart to illustrate one of the apertures which can accommodate the front or back end of a device such as a light curing gun.

DETAILED DESCRIPTION OF THE INVENTION

Figure 1:
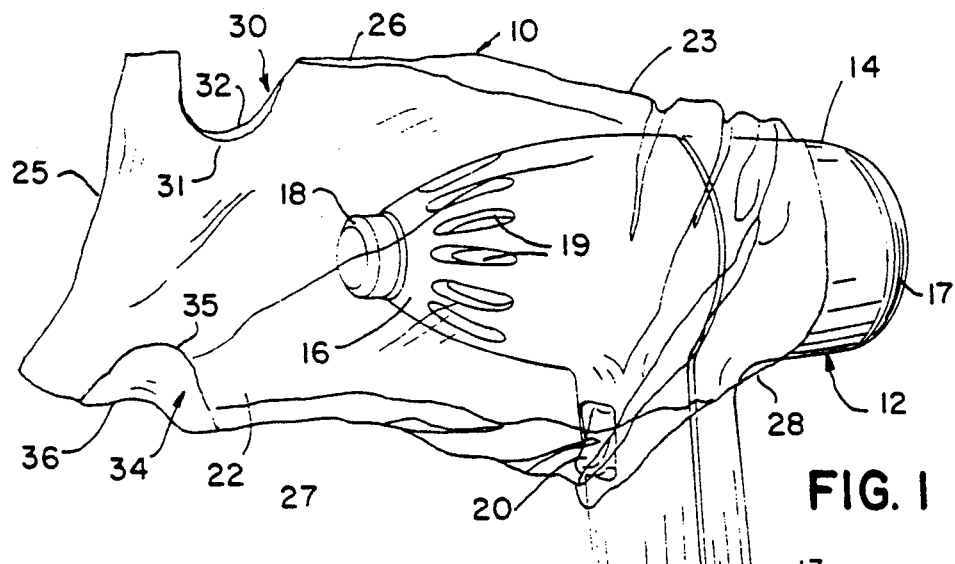
FIG. 1 is an illustrative perspective view of a light curing gun with a protective sleeve of the present invention shown being drawn on over the gun.

With reference to the drawings, a protective sleeve in accordance with the present invention is shown generally at 10 in FIG. 1 in the process of being pulled onto a light curing gun 12 of conventional design. The gun 12 is typical of curing guns utilized by dentists to cure certain light curable materials used to repair teeth. The typical gun 12 has a handle 13 adapted to be grasped by the dentist, and a generally cylindrical body 14 with a front end 16 and a back end 17 which extend away from the handle. The front end 16 of the gun includes a fitting 18 by which a light guide tube (not shown) is conventionally engaged on to the gun to guide the light from the gun to the desired position at the teeth of the patient. The guide tube is a replaceable part which is removed from the gun after use with a patient and separately sterilized. The gun 12 typically has vents 19 at the front end of the gun and vents (not shown) on the back end of the gun to allow cooling air into the interior of the gun.

Figure 2:
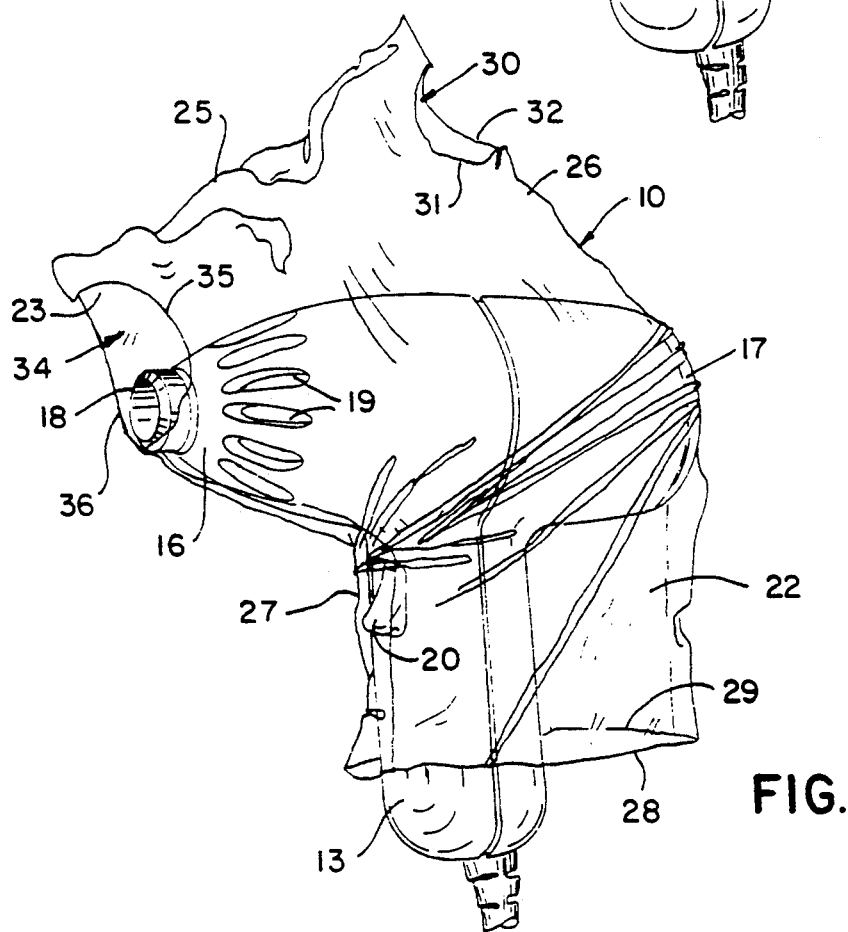
FIG. 2 is a further perspective view of a light curing gun with the protective sleeve of the invention drawn further onto the gun.
Figure 3:
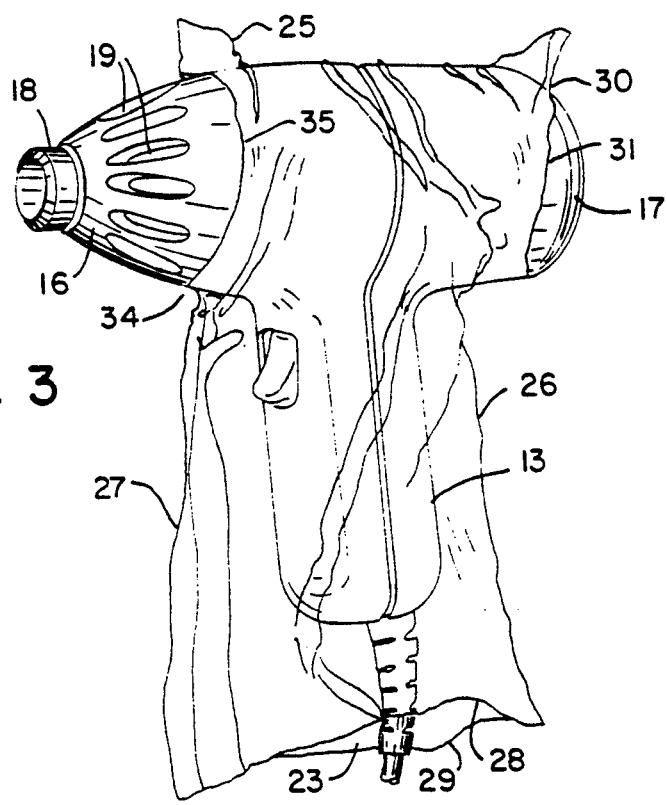
FIG. 3 is a perspective view of the protective sleeve of the invention drawn fully onto and covering a light curing gun.

The gun 12 itself does not come directly into contact with the patient, but the dentist or hygienist generally must hold the gun 12 by the handle 13 during the procedure. Thus, any contamination on the hand of the dentist from earlier work with the patient may be left on the handle 13 if it is unprotected. In addition to grasping the handle 13, the dentist must also operate the switch 20 which is typically mounted in the handle, and may incidently come into contact with the lower portions of the body 14 adjacent to the handle 13. The protective sleeve 10 of the present invention covers those portions of the gun 12 which will typically be contacted by the hand of the dentist during a procedure. The process of mounting the protective sleeve onto the gun is illustrated in the views of FIG. 1-3.

The sleeve 10 includes two panels 22 and 23, typically rectangular as shown, which are joined together at a top edge 25 and side edges 26 and 27. The bottom edges 28 and 29 (only the edge 28 is shown in FIG. 1) are not joined to one another, leaving an open bottom to the sleeve 10. The dentist inserts the gun 12 into the open bottom of the sleeve as illustrated in FIG. 1, and then draws the sleeve 10 down over the gun in the manner illustrated in FIG. 2. The inherent resiliency of the flexible plastic material (e.g., polyethylene film) of the sleeve allows it to stretch and distort as necessary to allow it to fit over the gun while it is being drawn into place.

An aperture 30 is formed in the panels at the side edge 26 at a position spaced away from but adjacent to the top edge 25. The aperture 30 is defined by adjoining notches 31 and 32 in the panels 22 and 23, respectively. Similarly, an opposed aperture 34 is formed at the side edge 26 at a position spaced away from but adjacent to the top edge 25, and is defined by adjoining notches 35 and 36 cut into the panels 22 and 23, respectively. As described further below, the notches 31, 32, 35 and 36 are preferably semi-circular or semi-elliptical in shape so that the entire apertures 30 and 34 are substantially circular or elliptical. The radius of the notches which define the apertures 30 and 34 is preferably chosen so that the apertures closely fit the front end and back end of a typical light curing gun, in the manner as illustrated in FIG. 3, allowing both the front end and the back end to be substantially fully exposed, with the sleeve 10 otherwise covering the body 14 of the curing gun at positions at which it would be contacted by the hand of the dentist.

Figures 4, 5, 6:
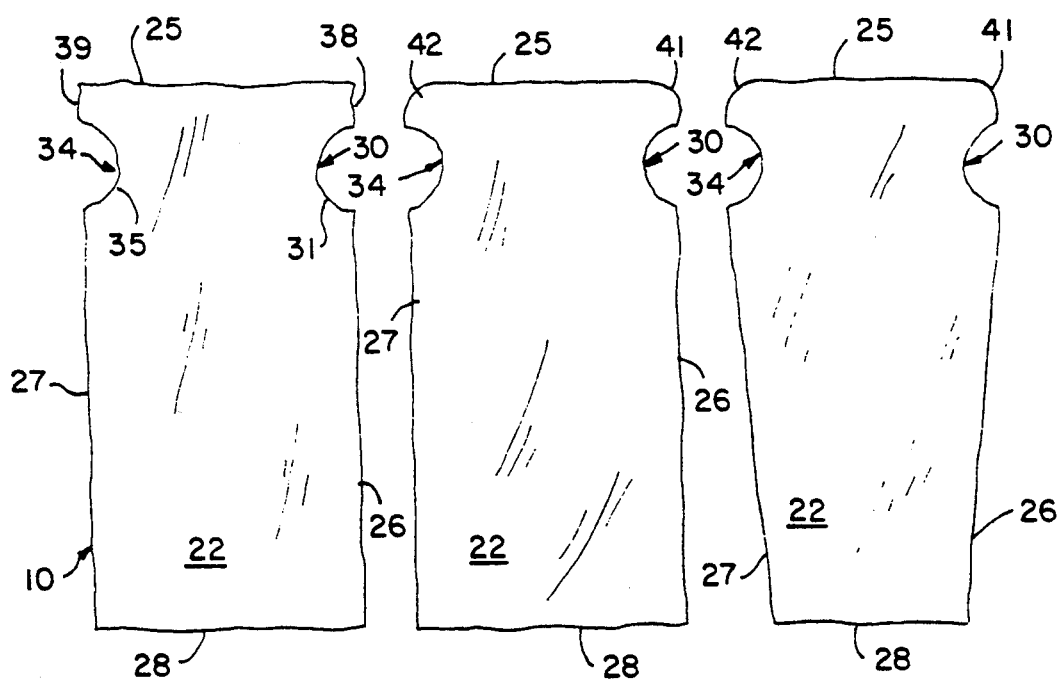
FIG. 4 is a plan view of a protective sleeve in accordance with the present invention.
FIG. 5 is a plan view of a modified embodiment of the protective sleeve of the present invention which has rounded top corners.
FIG. 6 is a plan view of a further modified embodiment of the protective sleeve of the invention having rounded top corners and tapered panels.

A plan view of the exemplary protective sleeve 10 is shown in FIG. 4, illustrating the semi-circular notches 31 and 35 in the front panel 22, respectively, which are matched by the adjoining notches 32 and 36 in the back panel 23. The notches 31 and 35 are formed in the side edges 26 and 27 at positions adjacent to, but, in a preferred embodiment, spaced away from the top edge 25 a short distance to leave short edge portions 38 and 39, typically ¼ to ½ inch in length. If desired, the notches 31 and 35 can be cut up to the edge 25, and, as described below, may be formed as cuts which extend from the edges 26 and 27 diagonally to cut across the top edge 25. Such cuts herein will be considered notches and define apertures in the panels of the sleeve which are adjacent to the top edge. For an application with a typical light curing gun, the notches 31, 32, 35 and 36 may have a radius in the range of ¾ inch to 1 inch, although it is understood that a larger or smaller radius may also be used as appropriate. The size of the apertures 30 and 34 is selected to best fit the body 14 of the gun: for example, for a light curing gun having a cylindrical body about 1 ¾ inches in diameter at its widest point, the apertures will preferably have a diameter slightly less than 1 ¾ inches.

In a preferred method of making the protective sleeve 10, an initial continuous sheet of polyethylene film, or any other suitable flexible plastic film, having a width preferably equal to twice the length of the side edges 26 and 27, may be folded over along a central crease line which will define the top edge 25, which thus integrally joins the film which will become the two panels 22 and 23. The folded over film is then cut to the desired width of the top edge 25 and the bottom edges 28 and 29, typically along cut lines substantially perpendicular to the crease line and the free edges, and then the panels are joined together at the side edges 26 and 27, for example, by heat sealing the panels together at these edges. The apertures 30 and 34 may then be formed in a die cutting operation wherein a die having circular knife edges, corresponding to the semi-circular notches 31, 32, 35 and 36, simultaneously cuts the notches 31 and 32 at the side edge 26, and simultaneously cuts the notches 35 and 36 at the side edge 27. Exemplary suitable dimensions for a sleeve for use with a typical hand held dentist light curing gun include rectangular panels with a width at the top edge 25 and bottom edges 28 and 29 of 5¼ inches, and a length along the side edges 26 and 27 of 10 inches.

The protective sleeve of the invention may be modified if desired without departing from the scope or spirit of the invention. Examples are illustrated in FIGS. 5 and 6. The protective sleeve of FIG. 5 is identical to the sleeve of FIG. 4 with the exception that the top edge 25 is joined to the side edges 26 and 27 by rounded radius corners 41 and 42, respectively. These radius corners may be formed by die cutting a radius into the corners of the protective sleeve and then heat sealing the edges of the panels at the corners. The sleeve of FIG. 6 is also shown illustratively having rounded corners 41 and 42, but has side edges 26 and 27 which are cut at a taper so that the bottom edges 28 and 29 are shorter than the top edge 25. A tapered sleeve of the form as shown FIG. 6 may be desirable in certain circumstances to provide a closer fit of the sleeve about the handle portion 13 of the light gun when the sleeve is in place on the light gun.

The protective sleeve of the invention may also have a variety of relative dimensions. For example, in the sleeve 50 shown in FIG. 7, the front panel 51 and back panel 52 have a substantially square shape, being joined together at side edges 53 and 54 and the top edge 57, and having bottom edges 55 and 56 which are not joined, with the edges 53, 54, 55, 56 and 57 all being substantially equal in length (e.g., a top edge of 7 ½ inches and side edges of 8 inches). Apertures 58 and 59 are formed at the side edges 53 and 54 by notches in the manner described above. The protective sleeve 50 shown in FIG. 7 may be utilized with types of dental equipment handled by the dentist during a procedure with a patient other than light curing guns. An example is illustrated in FIG. 8 in which the protective sleeve 50 is shown in place on a putty gun 61. The putty gun has a front end 62 which extends through the aperture 58, and a rear portion 64 which can extend out through the aperture 59. The putty gun 61 has a stationary handle 65 and a movable handle or trigger 66 which extends out from the stationary handle 65 and is grasped by the dentist to pull the trigger 66 toward the handle 65 to squeeze putty from the discharge tube 68 of the putty gun. The trigger handle 66 is then released and springs back out to the wide open position illustrated in FIG. 8. To accommodate the wide dimensions between the stationary handle 65 and the trigger handle 66 of the putty gun, the protective sleeve 50 is relatively wide so that it substantially entirely covers both the stationary handle portion 65 and the moveable handle portion 66. Nonetheless, because of the apertures 58 and 59 formed in the protective sleeve, the front end 62 and the back end 64 of the putty gun can extend out beyond the protective sleeve, since these portions of the gun are not contacted by the hand of the dentist, thus allowing the protective sleeve to be relatively closely fitted to the putty gun.

Another protective sleeve in accordance with the invention is shown at 70 in FIGS. 9 and 10. The sleeve 70 has two preferably rectangular flexible plastic panels 71 and 72, joined at a top edge 74, and at side edges 75 and 76, but not joined at bottom edges 78 and 79. Apertures 81 and 82, preferably circular, are die cut into the panels 71 and 72, respectively, at positions midway between the side edges 75 and 76 and adjacent to but spaced away from the top edge 74. The apertures 81 and 82 may be cut by a single circular die in a single step, cutting through both panels 71 and 72 so that the apertures adjoin one another when the panels are adjacent. As shown in FIG. 10, in which a light curing gun 12 is illustratively shown, when the sleeve 70 is drawn onto the gun 12, the front end 16 and the back end 17 of the gun extend out through the apertures 81 and 82.

A further embodiment of the protective sleeve of the invention is shown at 90 in FIGS. 11 and 12. The sleeve 90 has two rectangular panels 91 and 92 joined together at a top edge 94 and at side edges 95 and 96. The bottom edges 98 and 99 are not joined to allow access to the interior of the sleeve. Apertures 101 and 102 are formed in the panels of the sleeve by cutting off the corners of the sleeve adjacent the top edge by a cut which extends from the side edge 95 to the top edge 94 and from the side edge 96 to the top edge 94. Although straight cuts are shown in FIG. 11, it is understood that the cuts could be curved, e.g., semicircular. As shown in the side view of FIG. 12, the aperture 102 (and, similarly, the aperture 101) assumes a generally circular form as the panels 91 and 92 are drawn away from each other, as would occur as the front end 16 or back end 17 of a light curing gun were inserted through the apertures. The apertures 101 and 102 are seen to be on opposite sides of the sleeve to allow the front and back ends of a light gun to extend through these apertures while the remainder of the sleeve covers the handle and the remainder of the gun between the front and back ends.

It is understood that the invention is not confined to the particular embodiments set forth herein as illustrative, but embraces such modified forms thereof as come within the scope of the following claims.

What is claimed is:

1. A disposable protective sleeve adapted for covering hand held dental equipment of the type having a body with a front end and a back end and a handle extending from the body, comprising:

two flexible plastic film panels joined together at a top edge and joined together at two opposite side edges, the panels having bottom edges which are not joined to allow access to the interior of the protective sleeve, two apertures formed in the protective sleeve at positions opposite to each other in the sleeve which are nearer to the top edge of the sleeve than to the bottom edges, the apertures adapted to allow the front end and back end of the dental equipment to be passed therethrough while the sleeve covers the rest of the body and the handle.

2. The protective sleeve of claim 1 wherein the apertures are defined by adjoining notches in the panels at positions along the side edges of the sleeve which are spaced from the top edge.

3. The protective sleeve of claim 2 wherein the notches defining the apertures are rounded so that the adjoining notches together define a rounded aperture.

4. The protective sleeve of claim 3 wherein the notches in each panel are semi-circular so that the adjoining notches together define a circular aperture.

5. The protective sleeve of claim 4 wherein the maximum diameter of each notch and the diameter of the aperture formed by adjoining notches is about 1 ¾ inches to adapt the aperture to fit onto a standard light curing gun.

6. The protective sleeve of claim 2 wherein the side edges are substantially longer than the top and bottom edges.

7. The protective sleeve of claim 2 wherein the defining the apertures are spaced about ½ inch from the top edge.

8. The protective sleeve of claim 2 wherein the side edges taper inwardly from the top edge to the bottom edges, and wherein the top edge is longer than the bottom edges.

9. The protective sleeve of claim 2 wherein the size of the notches and the lengths of the top edge, side edges and bottom edges are selected to adapt the sleeve to fit a standard dentist's light curing gun so that a front end and a back end of a body of the light curing gun extend out through the apertures on the opposite sides of the sleeve and wherein a handle extending downwardly from the body of the light curing gun is covered by the protective sleeve.

10. The protective sleeve of claim 1 wherein the panels are integrally joined together at the top edge and are sealed together at the side edges.

11. The protective sleeve of claim 1 wherein the panels are formed of polyethylene film.

12. The protective sleeve of claim 1 wherein the top, bottom and side edges are about the same length.

13. The protective sleeve of claim 1 wherein each aperture is formed in a panel at a position midway between the side edges and spaced from the top edge.

14. The protective sleeve of claim 13 wherein each aperture is circular and the apertures in each panel adjoin one another when the panels are adjacent.

15. The protective sleeve of claim 1 wherein the apertures are defined by a cut through the panels extending from each side edge to the top edge.

16. A method of covering a dentist's light curing gun to help prevent cross contamination, the light curing gun being of the type having a substantially cylindrical body with a front end and a back end and a handle extending downwardly from the body, comprising the steps of:
  (a) providing a protective sleeve which comprises two flexible plastic film panels joined together at a top edge and joined together at two opposite side edges, the panels having bottom edges which are not joined to allow access to the interior of the protective sleeve, two apertures formed in the protective sleeve at positions opposite to each other in the sleeve which are nearer to the top edge of the sleeve than to the bottom edges;
  (b) drawing the protective sleeve onto the light gun such that the front end of the gun extends through one aperture of the sleeve and pulling the sleeve over the gun so that the back end of the gun extends through the other aperture of the sleeve, and so that the sleeve extends down over and covers the handle of the gun; and
  (c) after performing a procedure on the patient using the light gun, removing the protective sleeve from the light gun and disposing of the protective sleeve.

17. The method of claim 16 wherein the apertures in the protective sleeve are substantially circular and have a diameter that is substantially equal to but slightly less than the diameter of the cylindrical body of the gun such that as the sleeve is pulled onto the gun, the front end and the back end of the body of the gun extend through the apertures and the body of the gun stretches the plastic material of the protective sleeve to provide a tight fit of the protective sleeve on the gun.

18. A method of making a disposable protective sleeve for dental equipment such as light curing guns, comprising the steps of:
  (a) folding a sheet of plastic film in half about a crease line with the two halves of the sheet folded together with free edges opposite the crease line;
  (b) cutting the folded sheet into desired sizes along cut lines substantially perpendicular to the crease line and the free edges, with the cut edges defining the side edges of adjoining panels of a protective sleeve, the crease line defining the top edge of the protective sleeve, and the free edges defining the bottom edges of the protective sleeve;
  (c) heat sealing the cut edges of the protective sleeve together to form side edges of the sleeve; and
  (d) cutting through both adjoining panels of the sleeve at positions adjacent the top edge to define apertures on opposite sides of the sleeve.

19. The method of claim 18 wherein the sheet of plastic film is flexible polyethylene film.

20. The method of claim 18 wherein the step of cutting through both adjoining panels cuts notches in the panels at positions along the side edges of the panels spaced from the top edge.

21. The method of claim 20 wherein the notches are cut semi-circular so that the adjoining notches together define a circular aperture.

22. The method of claim 18 wherein the step of cutting through both adjoining panels cuts a substantially circular aperture in each panel at a position midway between the side edges and spaced from the top edge.

23. The method of claim 18 wherein the step of cutting through both adjoining panels cuts across the panels from each side edge to the top edge.

* * * * *

UNITED STATES PATENT AND TRADEMARK OFFICE
CERTIFICATE OF CORRECTION

PATENT NO. : 5,302,124
DATED : April 12, 1994
INVENTOR(S) : Lansing, et al.

It is certified that error appears in the above-indentified patent and that said Letters Patent is hereby corrected as shown below:

Column 6, line 53, after "wherein the", insert --notches--.

Signed and Sealed this

Twenty-eight Day of February, 1995

Attest:

BRUCE LEHMAN

*Attesting Officer*     *Commissioner of Patents and Trademarks*